United States Patent
Daldrup-Link

(10) Patent No.: US 9,579,349 B2
(45) Date of Patent: Feb. 28, 2017

(54) IN VIVO IRON LABELING OF STEM CELLS AND TRACKING THESE LABELED STEM CELLS AFTER THEIR TRANSPLANTATION

(71) Applicant: The Board of Trustees of the Leland Stanford Junior University, Palo Alto, CA (US)

(72) Inventor: Heike E. Daldrup-Link, San Francisco, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 453 days.

(21) Appl. No.: 14/161,315

(22) Filed: Jan. 22, 2014

(65) Prior Publication Data

US 2014/0205575 A1    Jul. 24, 2014

Related U.S. Application Data

(60) Provisional application No. 61/755,283, filed on Jan. 22, 2013.

(51) Int. Cl.
   *A61K 35/28* (2015.01)
(52) U.S. Cl.
   CPC .................................. *A61K 35/28* (2013.01)
(58) Field of Classification Search
   None
   See application file for complete search history.

(56) References Cited

PUBLICATIONS

Amsalem et al., Iron-Oxide Labeling and Outcome of Transplanted Mesenchymal Stem Cells in the Infarcted Myocardium, Circulation, 2007, vol. 116, p. I38-I45.*
Neuwelt et al., The potential of Ferumoxytol Nanoparticle MRI, Perfusion, and Angiography in CNS Malignancy: A Pilot Study, Neurosurgery 60:601-612, 2007.*
Stuckey et al, Iron Particles for Noninvasive Monitoring of Bone Marrow Stromal Cell Engraftment into, and Isolation of Viable Engrafted Donor Cells from, the Heart, Stem Cells, 2006:24, pp. 1968-1975.*
Castaneda et al, Labeling Stem Cells with Ferumoxytol, an FDA-Approved Iron Oxide Nanoparticle, Journal of Visual Experimentation, (57), Nov. 4, 2011.*
Nedopil, MR Signal Characteristics of Viable and Apoptotic Human Mesenchymal Stem Cells in MASI for Treatment of Osteoarthritis, Invest Radiol. Oct. 2010; 45(10): 634-640.*
Shapiro, Long Term Cellular MR Imaging Using Micron Sized Iron Oxide Particles, Proc. Intl. Soc. Mag. Reson. Med. 11 (2004).*
Seneterre, Bone Marrow: ultrasmall superparamagnetic iron oxide for MRI imaging, Radiology, May 1991, vol. 179, Issue 2.*
Khurana, Intravenous Ferumoxytol Allows Noninvasive MR Imaging Monitoring of Macrophage Migration into Stem Cell Transplants, Radiology, vol. 264, No. 3, Sep. 2012.*

(Continued)

*Primary Examiner* — Taeyoon Kim
*Assistant Examiner* — Srikanth Patury
(74) *Attorney, Agent, or Firm* — Lumen Patent Firm

(57) ABSTRACT

Intravenous ferumoxytol is used to effectively label mesenchymal stem cells (MSCs) in vivo and is used for in vivo tracking of stem cell transplants with magnetic resonance (MR) imaging. The method eliminates risk of contamination and biologic alteration of MSCs associated with ex-vivo-labeling procedures.

9 Claims, 12 Drawing Sheets
(11 of 12 Drawing Sheet(s) Filed in Color)

(56) References Cited

PUBLICATIONS

Pumping iron: new way of tracking transplanted stem cells uses anemia drug (Jul. 15, 2013, online). https://blog.cirm.ca.gov/2013/07/15/pumping-iron-new-way-of-tracking-transplanted-stem-cells-uses-anemia-drug/.

Stem Cell Tracking Made Possible With Common Anemia Drug at Stanford (Jul. 15, 2013, online) http://www.huffingtonpost.com/2013/07/15/stem-cell-tracking-anemia-drug-ferumoxytol_n_3600419.html#httpwwwhuffingtonpostcom20130715stem-cell-tracking-anemia-drug-ferumoxytol_n_3600419html.

MR Imaging Plays Pivotal Role in Stem Cell Tracking (Dec. 1, 2013, online) http://www.rsna.org/NewsDetail.aspx?id=10729.

\* cited by examiner

IN VIVO IRON LABELING OF STEM CELLS AND TRACKING THESE LABELED STEM CELLS AFTER THEIR TRANSPLANTATION

CROSS-REFERENCE TO RELATED APPLICATIONS

This application claims priority from U.S. Provisional Patent Application 61/755,283 filed Jan. 22, 2013, which is incorporated herein by reference.

STATEMENT OF GOVERNMENT SPONSORED SUPPORT

This invention was made with Government support under contract no. 2R01AR054458-05 awarded by the National Institutes of Health (NIH). The Government has certain rights in this invention.

FIELD OF THE INVENTION

This invention relates to in vivo iron labeling of stem cells and subsequent tracking of these stem cells with magnetic resonance imaging after their transplantation.

BACKGROUND OF THE INVENTION

Each year, arthritis results in 44 million outpatient visits, 992100 hospitalizations, and 700000 knee replacement procedures (www.cdc.gov/arthritis). The need for knee replacement is rapidly increasing, with 3.48 million expected procedures by 2030. However, artificial implants are associated with potential complications, such as periprosthetic fractures, loosening, and metal sensitivity. Even in the absence of complications, the lifetime of an artificial prosthesis is limited to approximately 10 years as the implant wears out.

Cell transplants, particularly stem cell-scaffold nanocomposites, could overcome these problems by providing long-term biologic restoration of joint defects. Bone marrow-derived mesenchymal stem cells (MSCs) have been established as a promising source for stem cell-mediated joint repair in a clinical setting. MSCs can be obtained with a bone marrow aspirate, are expanded in vitro, and can differentiate into all joint components. However, interactions between transplanted MSCs and the patient's host environment are still poorly understood.

To monitor successful engraftment and recognize complications such as graft failure or tumor formation, MSC therapies require tracking of the transplanted stem cells. In the past, stem cell tracking has been achieved on the basis of the concept of ex vivo contrast agent labeling. This approach requires multiple ex vivo manipulations of stem cells between their harvest and transplantation.

Clinical translation of ex vivo-labeling procedures is complicated from a regulatory point of view as these manipulations greatly enhance the risk of cell sample contamination, alterations in stem cell biology, or in vivo side effects from added transfection agents. Most transfection agents (LIPOFECTAMINE 2000 [Invitrogen, Carlsbad, Calif.] or poly-L-lysine [Sigma-P4707; Sigma-Aldrich, St Louis, Mo.]) are not U.S. Food and Drug Administration (FDA) approved. In addition, some ultra-small super-paramagnetic iron oxide-transfection agent combinations have induced cytotoxic effects or altered the stem cell biology.

Accordingly, the art is in need of more immediately clinically applicable methods for stem cell labeling, which would not require ex vivo manipulations of harvested cells and which would eliminate the need for transfection agents, that then could be used to track transplanted MSCs. The present invention addresses this need.

SUMMARY OF THE INVENTION

Instead of conventional labeling ex vivo in cell culture, the method of this invention is an in vivo labeling method of mesenchymal stem cells (MSCs) with intravenous injection of ferumoxytol (Feraheme; AMAG Pharmaceuticals, Lexington, Mass.), a Food and Drug Administration (FDA)-approved intravenous iron supplement. The in vivo iron labeling or uptake by the stem cells is a result of phagocytosis or endocytosis following the intravenous injection. With in vivo labeling, iron uptake was found to be superior to comparative ex vivo labeling, and labeled, collected MSCs that were subsequently implanted into the knees of rats with an induced osteochondral defect could be readily detected on T2-weighted MR images for at least 4 weeks after transplantation.

Specifically, a clinical stem cell therapy method is provided for in vivo and noninvasively monitoring of stem cell implants. Iron oxide nanoparticles are intravenously injected into a subject to achieve in vivo phagocytotic (or endocytotic) iron labeling of stem cells (e.g. mesenchymal stem cells). In one example, the subject is a human and the iron oxide nanoparticles are dosed at 28 mg Fe/kg. In another example, the subject is an animal (e.g. a rodent) and the iron oxide nanoparticles are dosed at 5-10 mg/kg for the subject. It is noted that this labeling or uptake of iron by the stem cells occurs in vivo without any addition of a transfection agent. It is also noted that the in vivo labeling does not use any ex vivo labeling or ex vivo manipulations to the stem cells.

After one to three days upon the intravenous injection, iron-labeled stem cells are harvested from the bone marrow of the subject. In one example, directly after the harvesting the harvested iron-labeled stem cells are transplanted into the same subject or a different subject. In another example, the harvested iron-labeled stem cells can be expanded ex vivo. The transplantation in that case will then take place three to four weeks after the ex vivo expansion. Transplantation could take place in an organ, or specifically in a joint, a brain, a heart, a liver, or a pancreas.

In vivo and noninvasively monitoring of the transplanted stem cells using magnetic resonance imaging can now take place to determine the accuracy of stem cell transplants, the immediate engraftment pattern, and the long-term retention at the target allows us to optimize stem cell treatment protocols. The in vivo labeling would eliminate safety concerns associated with ex vivo stem cell manipulations and enable in vivo detection of lost or rejected stem cell transplants early enough for corrective actions.

While the specific embodiment pertains to a mechanical osteochondral defect as the therapeutic target, it is important to realize that this is just an example application. Being able to MR track iron-labeled MSCs safely and effectively will have myriad clinical applications to a variety of other stem cell transplants in other target organs, including but not limited to stroke, myocardial infarct, and a range of autoimmune diseases including multiple sclerosis and type I diabetes mellitus.

BRIEF DESCRIPTION OF THE DRAWINGS

The patent of application file contains at least one drawing executed in color. Copies of this patent or patent application publication with color drawing(s) will be provided by the Office upon request and payment of the necessary fee.

In FIG. 5A, fluorescence microscopy demonstrates green fluorescence signal of in vivo FITC-ferumoxytol-labeled cells. The fluorescence signal slowly declines over time. Corresponding T2 relaxation time maps of cell pellets in test tubes show shortening of T2 relaxation times of in vivo-labeled cell pellets compared with unlabeled control pellets, which also decreases slowly over time. Color spectrum=color scale for T2 time (milliseconds) that signifies MR signal intensity of the pellet; the more iron (ferumoxytol) the cells contain, the lower the T2 value. LIV=labeled in vivo, C=control cells. FIG. 5B shows quantitative T2 relaxation times of in vivo-labeled cell pellets and unlabeled control cells at weeks 1, 2, 3, and 4 after extraction from bone marrow show shortening of T2 relaxation times of in vivo-labeled cell pellets compared with unlabeled control cells. FIG. 5C shows iron content per cell of in vivo-labeled cells, ex vivo-labeled cells, and control cells, as measured by inductively coupled plasma optical emission spectrometry. In vivo-labeled cells show significantly higher iron uptake at day 7 compared with ex vivo-labeled cells and control cells. Data are displayed as means and standard errors (error bars) of triplicate samples per experimental group, with $4\times10^5$ cells per sample.

In FIG. 7A, representative T2 relaxation time maps show shortened T2 relaxation times of in vivo-labeled MSC transplants (arrow) compared with unlabeled control transplants (arrowhead) at weeks 0, 2, and 4 after transplantation. The T2 signal effect of labeled transplants slowly decreases over time. Color spectrum=color scale for T2 time (milliseconds) that signifies MR signal intensity of the implant; the more iron (ferumoxytol) the implanted cells contain, the lower the T2 value. In FIG. 7B, corresponding T2 relaxation times show significantly shorter T2 values of in vivo-labeled transplants compared with unlabeled control transplants up to 4 weeks after implantation. Data are displayed as means and standard errors (error bars) of six animals in each group.

DETAILED DESCRIPTION

Figure 1:
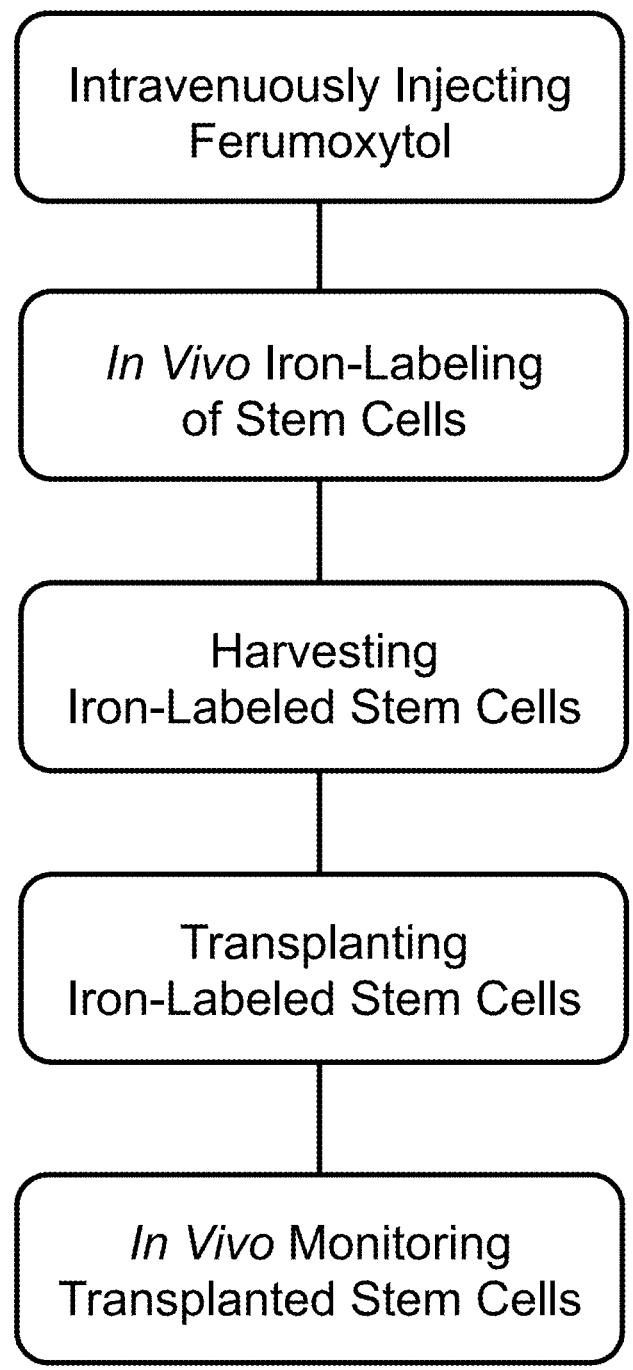
FIG. 1 shows a flow diagram of the clinical stem cell therapy method according to an exemplary embodiment of the invention.

The approach of the method of the present invention (FIG. 1) relies on intravenous administration of an FDA-approved iron supplement ferumoxytol (Feraheme; Advanced Magnetics, Cambridge, Mass.) to a stem cell donor prior to stem cell harvest from bone marrow. Ferumoxytol is composed of iron oxide nanoparticles, which are taken up by the reticuloendothelial system in vivo, and which provide a strong signal intensity effect on magnetic resonance (MR) images. Accordingly, intravenously injected ferumoxytol would be taken up by mesenchymal stem cells (MSCs) in bone marrow, would be retained in the cells through harvesting (and in one example ex vivo expansion) and allow for sensitive in vivo MSC detection with MR imaging after transplantation into osteochondral defects. The method provided herein demonstrates intravenous ferumoxytol administration as a clinically applicable iron supplement to effectively label MSCs in vivo and for tracking of stem cell transplants.

Materials and Methods

In Vivo MSC Labeling

Sixteen 6-8-week-old Sprague-Dawley rats (Charles River, Wilmington, Mass.) served as MSC donors: Seven rats remained untreated, while nine rats were injected intravenously with ferumoxytol (n=7) or fluorescein isothiocyanate (FITC) (Fisher Scientific, Pittsburgh, Pa.) conjugated ferumoxytol (n=2) (hereafter referred to as FITC-ferumoxytol) at a dose of 28 mg of iron per kilogram. The details for synthesis are included infra in section Synthesis of FITC-conjugated ferumoxytol. This dose had been shown to elicit significant MR signal intensity effects of the bone marrow in rodents in previous studies. Seven athymic Sprague-Dawley rats served as MSC recipients and underwent MR imaging up to 4 weeks after stem cell transplantation.

MSC Extraction and Cultivation

Figure 2:
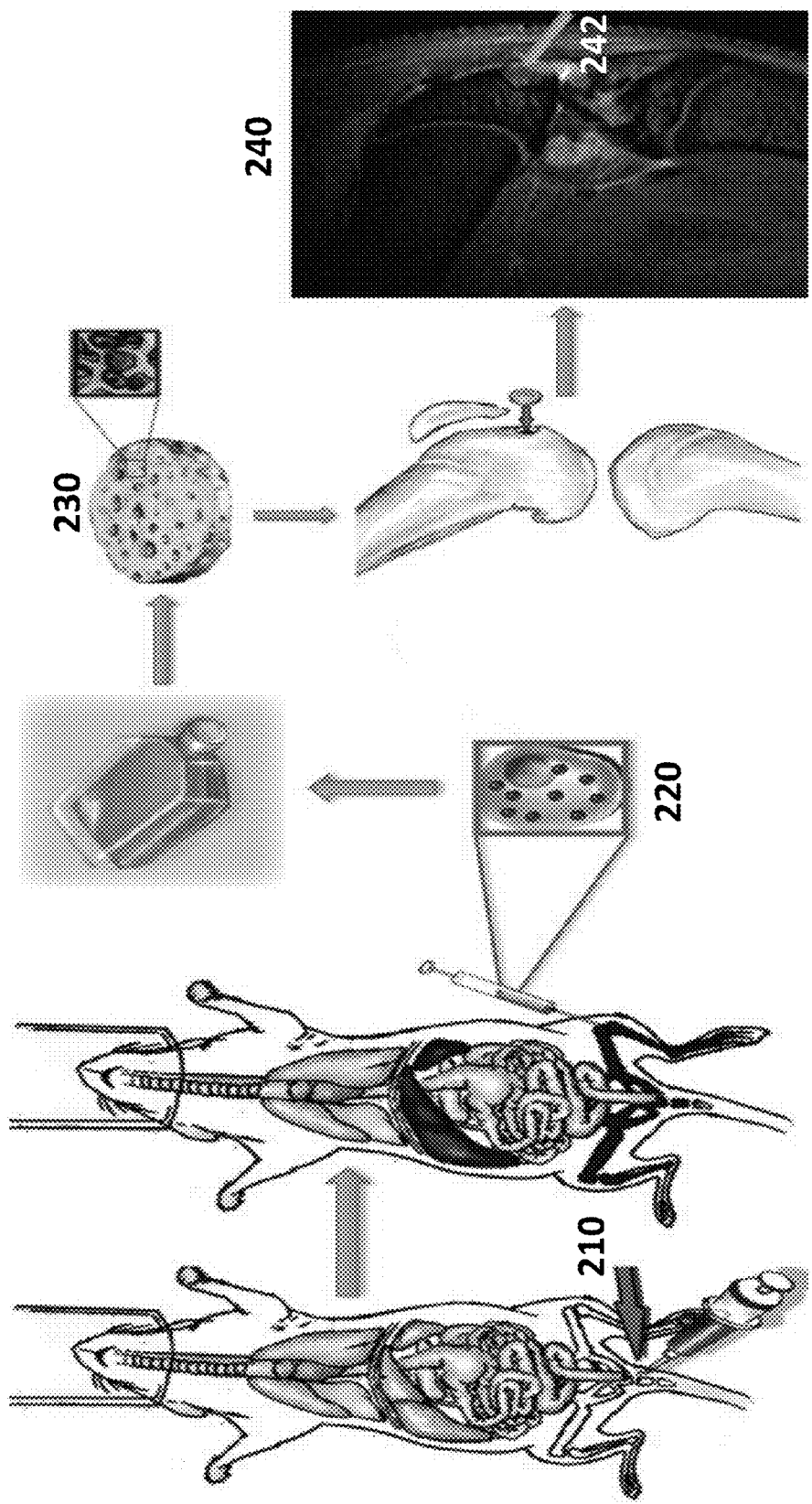
FIG. 2 shows according to an exemplary embodiment of the invention in vivo ferumoxytol labeling of bone marrow mesenchymal stem cells (MSCs) and subsequent in vivo tracking of transplanted MSCs with MR imaging. The method relies on intravenous injection of ferumoxytol (red arrow 210) and its phagocytosis by cells in the reticuloendothelial system (liver, spleen, and bone marrow). Ferumoxytol-labeled bone marrow cells are harvested by using bone marrow aspiration (red square insets 220) and in this example are expanded in vitro for 7 days. Inset 230: Cells seeded on a scaffold. The labeled cells are then seeded in an agarose scaffold and implanted in an osteochondral defect of the distal femur. Sagittal T2-weighted MR image 240 (repetition time msec/echo time msec, 4000/15, 30, 45, 60) shows monitoring of transplant engraftment (arrow 242).

Donor Sprague-Dawley rats were euthanized by means of $CO_2$ inhalation 2 days after intravenous ferumoxytol injection to allow sufficient time for phagocytosis by reticuloendothelial system cells, considering a blood half-life of 67 minutes in rodents. Both femurs and tibias were isolated. The epiphyses were removed, and the bone marrow was flushed with Dulbecco's modified Eagle's medium (Invitrogen), supplemented with 10% fetal bovine serum (Invitrogen). The cells were separated on a cell strainer (BD, Franklin Lakes, N.J.) to prevent adding any coagulated tissue in the culture flask, centrifuged at 1800 rpm for 10 minutes and resuspended in 1 mL of ammonium-chloride-potassium buffer (ACK Lysing Buffer; Invitrogen) for 2 minutes, washed with phosphate-buffered saline, and spun again at 1800 rpm for 10 minutes. The cells were plated in a flask with a 75-cm$^2$ flask area (culture surface area) in full media, supplemented with 50 pg of fibroblast growth factor (Gibco, Gaithersburg, Md.) and maintained at 37° C. with 5% $CO_2$ for 7 days FIG. 2). The medium was replaced every 72 hours or when cells reached confluence. Nonadherent hematopoietic stem cells, red blood cells, and white blood cells were eliminated with every change in culture medium, leaving the adherent and expanding MSCs behind. This direct adherence method has shown improved efficiencies for MSC selection, compared with density gradient centrifugation.

All in vivo experiments were performed with cells at passage 0 (day 7 of labeling). In vitro studies involved evaluation of ferumoxytol-labeled cells and unlabeled cells until day 28, corresponding to passage 0-6. Viability assays were performed at each passage by using the trypan blue exclusion test with the use of an automatic cell counter (Countess; Invitrogen).

MSC Immunostaining

Day 7 cells were fixed with 10% formalin (BDH, West Chester, Pa.) and plated on chamber slides at a concentration of cells of 60 000/cm$^2$. Immunohistochemical stains against CD105 for MSC (Endoglin M-20; Santa Cruz Biotechnology, Dallas, Tex.) and CD68 for macrophages (Abcam, Cambridge, Mass.) were performed, and slides were counterstained by using 49,6-diamidine-2-phenylindole. Two researchers counted the number of CD105- and CD68-positive cells separately, and data were averaged over 12 high-power fields (magnification, 320) for each stain.

Evaluation of Ferumoxytol Uptake by MSCs

MSCs labeled with FITC-ferumoxytol in vivo or FITC-conjugated ferumoxytol and protamine (hereafter referred to as FITC-ferumoxytol-protamine) ex vivo, as well as untreated control cells, were evaluated for the presence or absence of green FITC fluorescence by using a fluorescence microscope (Olympus BH-2; Scion, Frederick, Md.) and image processing software (Metamorph; Molecular Devices, Sunnyvale, Calif.). Cell samples were also analyzed by using confocal microscopy (LSM 510; Carl Zeiss, Thornwood, N.Y.). Fluorescence intensities and three-dimensional 3D) intensity plots were calculated with ImageJ software (http://rsbweb.nih.gov/ij/) by using an established protocol and a threshold of 20 fluorescence units.

To evaluate the compartmentalization of iron oxide nanoparticles in MSCs, 400000 cells (in triplicate) labeled in vivo with ferumoxytol, labeled ex vivo with ferumoxytol and protamine, or untreated (control cells) were processed for electron microscopy. Sections of 100-nm thickness of resin-embedded cell samples were placed on 100-mesh Formvar-coated copper grids (FCF2010-Cu; Electron Microscopy Sciences, Hatfield, Pa.) and imaged using a transmission electron microscope (Tecnai F20 X-Twin; FEI, Hillsboro, Oreg.).

In addition, triplicate samples of in vivo-labeled MSCs (at days 7 and 14), ex vivo-labeled MSCs, and unlabeled control cells underwent inductively coupled plasma optical emission spectrometry for quantification of intracellular iron content. The iron content per sample was divided by cell concentration to provide iron content per cell.

Evaluation of in Vitro MR Signal Intensity Effects of Ferumoxytol-Labeled MSCs

Triplicate samples of 400000 labeled and unlabeled control cells at days 7, 14, 21, and 28 after extraction were suspended in 10 mL of agarose scaffold (Sigma-Aldrich) and underwent MR imaging with a 7-T animal MR imaging unit ("microSigna 7.0" collaboration between GE Health-care [Waukesha, Wis.] and Varian [Walnut Creek, Calif.]) using a single-channel transmit-receive partial birdcage radiofrequency coil. Sagittal MR images of the cell samples were obtained with a fast spin-echo sequence (3000/30) and a multiple-echo spin-echo sequence (4000/15, 30, 45, 60), using a field-of-view of 3.5 3 3.5 cm, a matrix of 256 3 256 pixels, and a section thickness of 0.5 mm. Pixelwise T2 relaxation time maps generated by using custom research software (Cinetool; GE Global Research Center, Niskayuna, N.Y.) were used to measure T2 relaxation times of each sample through operator-defined regions of interest. Following MR imaging, the chondrogenic potential of the cell samples was evaluated.

In Vivo MR Tracking of Ferumoxytol-Labeled MSCs

Next, in vivo-labeled MSCs were implanted into osteochondral defects of knee joints of seven recipient rats (14 knees). Osteochondral defects were created in the distal femoral trochlear groove of both knee joints by using a microdrill (Ideal, Sycamore, Ill.). In each rat, $1 \times 10^6$ in vivo ferumoxytol-labeled MSCs in an agarose scaffold were implanted into the right femur and $1 \times 10^6$ unlabeled MSCs in an agarose scaffold were implanted into the left femur. MSC transplants were evaluated with MR imaging immediately after stem cell transplantation (n=7), as well as 2 weeks (n=7) and 4 weeks (n=6) after transplantation, by using the same MR technique described above. T2 relaxation time maps were generated. After the last MR image was obtained, at 2 weeks (n=1) and 4 weeks (n=6) after transplantation, animals were sacrificed, and specimens were processed for histopathologic correlations, which included hematoxylin-eosin, 3,3' diaminobenzidine-Prussian blue, and Alcian blue staining Immunohistochemical staining against CD105 (Endoglin M-20; Santa Cruz Biotechnology) and CD68 (Abcam) were performed to evaluate MSCs and macrophage populations in osteochondral defects, respectively.

Statistical Analysis

T2 relaxation times and iron uptake data were compared for significant differences between different experimental groups by using t tests. Within each group, changes in MR data over time were examined by using ordinary least squares linear regression analyses. The t tests, analysis of variance, and linear models were computed by using the t test and the aov and lm functions in R (version 2.15.2) respectively. Because the right and left knees of each rat contained different implants, it was assumed that MR images of each rat's knee were independent observations. To examine the possibility that data from the same rats were dependent (e.g., different rats metabolized the iron labels at different rates), multilevel models were fit to MR data by using the R package lme4 (version 0.999999-0), with specifications identical to each linear model. A variable that identified each rat was added as a random effect, and the fit of each model was compared. In each case, the model fits were not significantly different. For all analyses, a P value of less than 0.05 was considered to indicate a significant difference among different experimental groups or different times of observation.

Results

MSC Immunostaining

Figure 3:
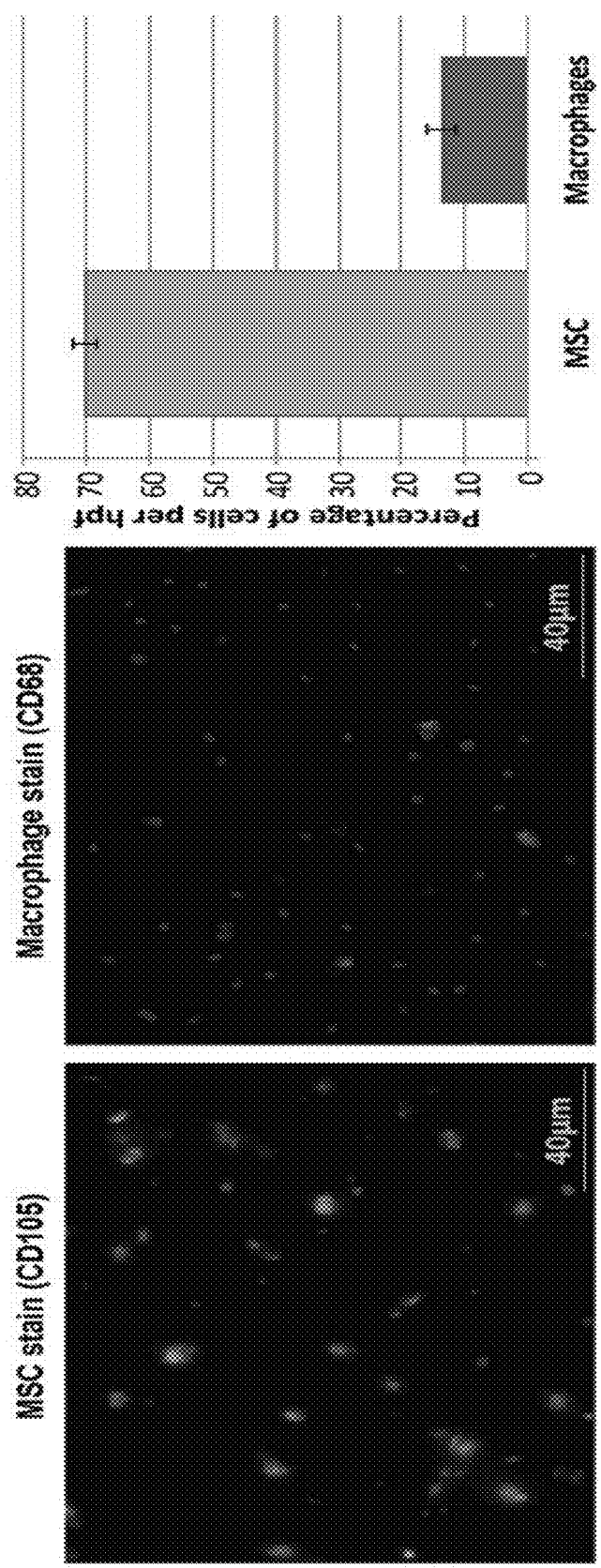
FIG. 3 shows according to an exemplary embodiment of the invention, that the majority of in vivo labeled cells, that had been harvested from bone marrow and expanded in MSC-selective culture for 7 days, are MSC. CD105 (one of several MSC markers) and CD68 (macrophage marker) stains of bone marrow-derived cells after 7 days of MSC-selective culture. Evaluation of 3000 4',6-diamidine-2-phenylindole-positive cells in 12 high-power fields (magnification, 320) revealed a mean of 70.2%+/−1.9 MSCs (CD105-positive cells=green) and of 13.5%+/−2.3 macrophages (CD68-positive cells=red) per high-power field. 4',6-Diamidine-2-phenylindole (blue) counterstain visualized cell nuclei of all cells in these samples, including CD105- and CD68-positive cells and other cells. hpf=High-power field.

The yield from bone marrow aspirates was approximately 400 million cells for both ferumoxytol-injected animals and untreated control animals. MSC-selective culture led to separation of MSCs (attached to the flask) from other cells (in solution). At day 7, approximately 5 million cells remained attached to the flask. Staining in a mean of 181.3 day 7 cells per high-power field 6 7.9 (standard deviation) (70.2% 6 1.9) was positive for CD105, while staining in only a mean of 33.4 day 7 cells per high-power field 6 5.6 (13.5% 6 2.3) was positive for CD68 (FIG. 3). Of note, freshly extracted MSCs are small in size and slowly expand in culture. Expansion in cell culture is needed prior to ex vivo labeling to achieve satisfactory cell survival. Ex vivo labeling requires 4 hours of fetal bovine serum deprivation, exposure to a transfection agent (protamine), and multiple centrifugation steps that freshly extracted cells can hardly withstand (FIGS. 3-4).

Evaluation of Ferumoxytol Uptake by MSCs

Figure 4:
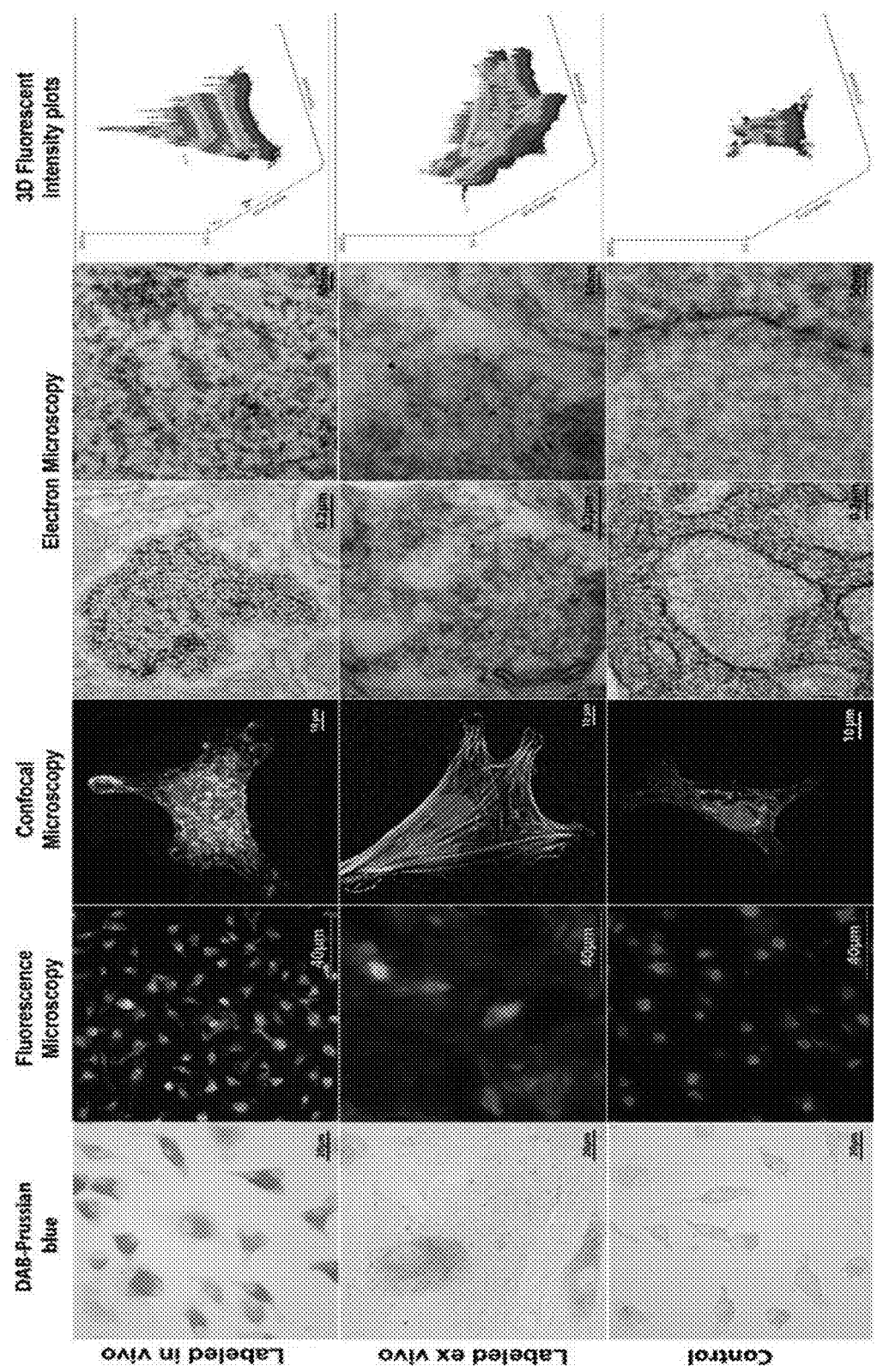
FIG. 4 shows according to an exemplary embodiment of the invention ferumoxytol uptake by MSCs, labeled in vivo via ferumoxytol injection or labeled ex vivo via protamine transfection. 3,3'Diaminobenzidine (DAB)-Prussian blue staining, fluorescence microscopy, confocal microscopy, and corresponding 3D fluorescent plots show intracellular iron uptake for in vivo- and ex vivo-labeled cells, with a higher effectiveness of the in vivo-labeling technique compared with ex vivo labeling. Transmission electron microscopy images show compartmentalization of iron oxide nanoparticles (arrows) in secondary lysosomes in in vivo- and ex vivo-labeled cells, with relatively higher intralysosomal nanoparticle quantities in the in vivo-labeled cells. Nonlabeled control cells are shown for comparison. 4',6-Diamidine-2-phenylindole (blue), rhodamine (red), and FITC (green) signals represent nuclei, cytoskeleton, and iron nanoparticles, respectively. Colocalization of red and green signals indicates the presence of iron nanoparticles in the cytoplasm. This colocallization of green and red signals results in yellow signal for high concentrations of iron nanoparticles in in vivo-labeled cells and orange color for smaller concentrations of iron nanoparticles in ex vivo-labeled cells. The 3D plots reveal the amount of FITC-positive signal (iron nanoparticles) as peaks per pixel in each cell.
Figure 9:
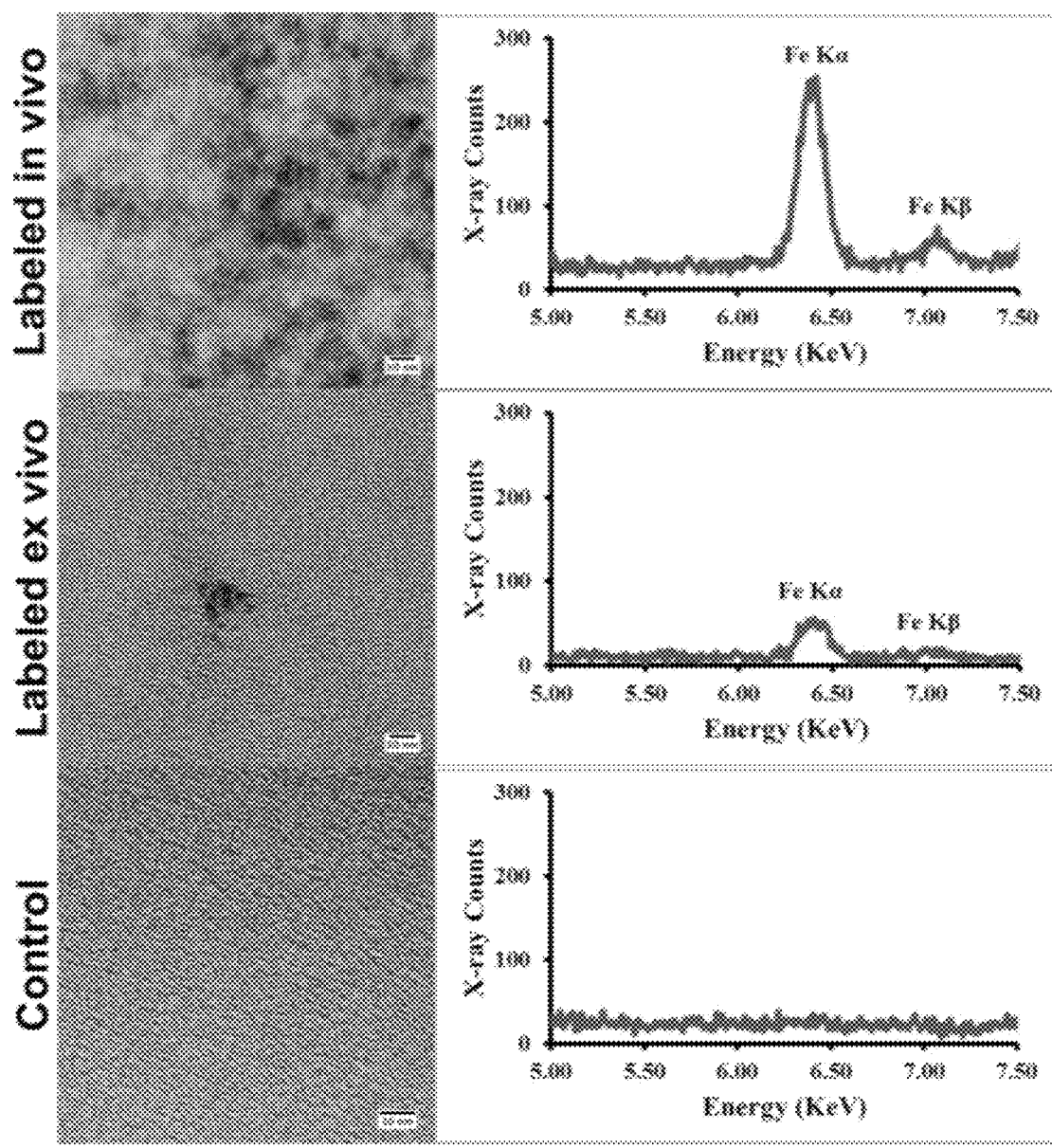
FIG. 9 shows according to an exemplary embodiment of the invention nanoparticle characterization by energy dispersive x-ray spectroscopy. High magnification transmission electron microscopy images confirming presence of iron nanoparticles in in vivo and ex vivo labeled lysosomes and corresponding energy dispersive spectrums showing higher iron content in in vivo labeled samples.

MSCs labeled with FITC-ferumoxytol demonstrated cellular iron oxide uptake at fluorescence and confocal microscopy, without apparent differences in cytoplasmic nanoparticle compartmentalization between in vivo- or ex vivo-labeled cells (FIG. 4). Electron microscopy localized iron oxide nanoparticles in secondary lysosomes (FIG. 4). However, confocal and electron microscopy examinations revealed a higher quantity of iron oxide nanoparticles in in vivo-labeled MSCs compared with ex vivo-labeled MSCs (FIG. 4, FIG. 9). The fluorescence intensity of in vivo-labeled cells ($\Delta$ intensity=47.025) was 3.2 times higher compared with the fluorescence intensity of ex vivo-labeled cells ($\Delta$ intensity=14.527, P=0.00005). The 3D plots, representing FITC-ferumoxytol concentrations as peaks per pixel on the area of individual cells (FIG. 4) confirm that labeled in vivo cells are smaller in size and contain more iron nanoparticles than labeled ex vivo cells. Both labeling techniques showed significantly higher fluorescence intensities as compared with control cells (P<0.001) FIG. 4.

Evaluation of in Vitro MR Signal Intensity Effects of Ferumoxytol-Labeled MSCs

Figure 5A:
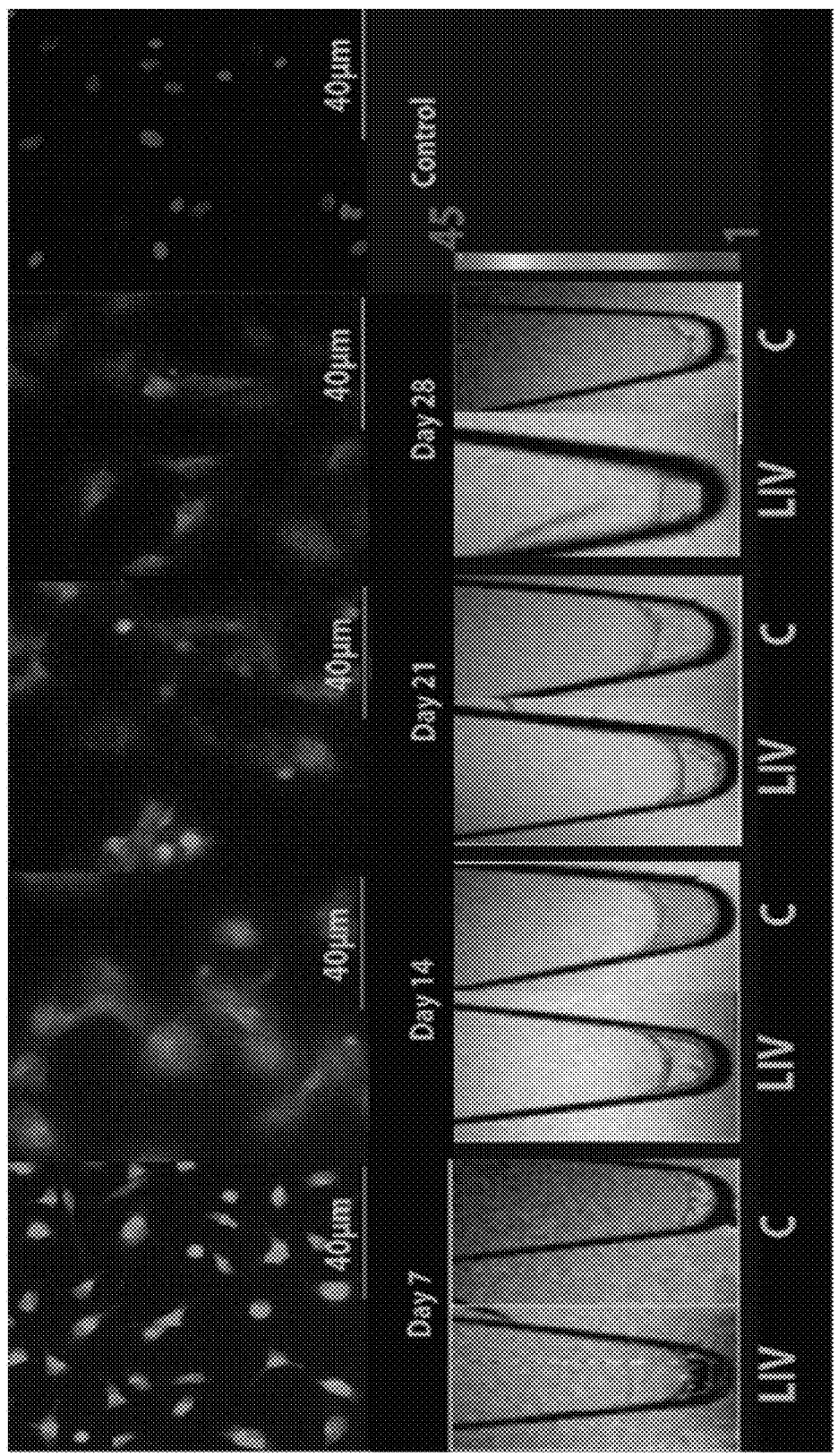
FIGS. 5A-C show according to an exemplary embodiment of the invention longitudinal in vitro evaluations of FITC-ferumoxytol-labeled MSCs.
Figure 5B:
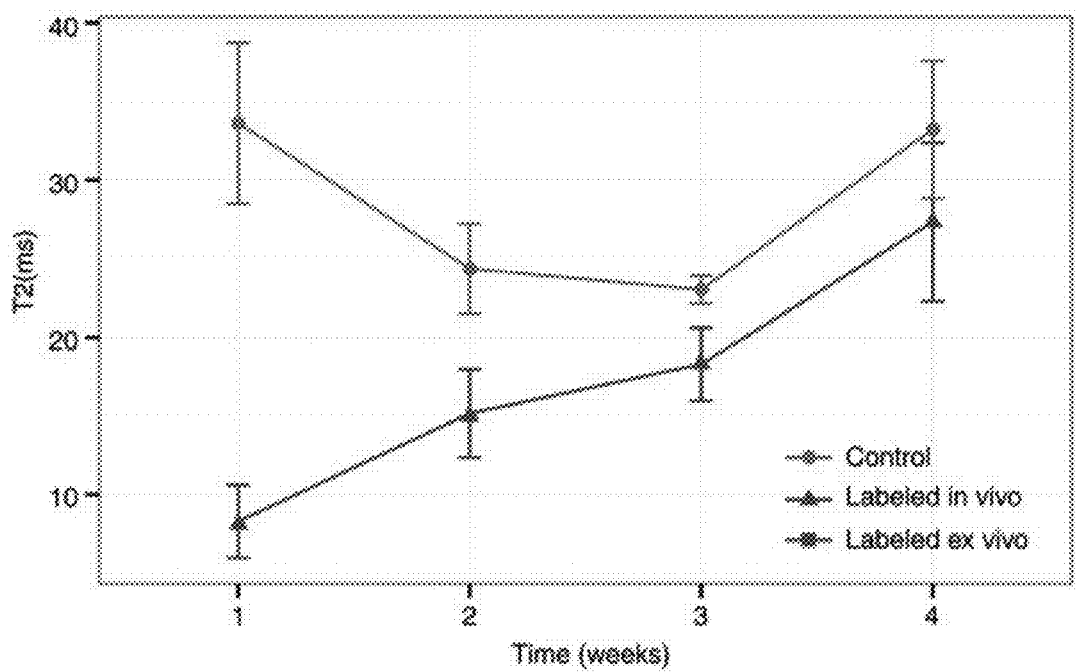
Figure 5C:
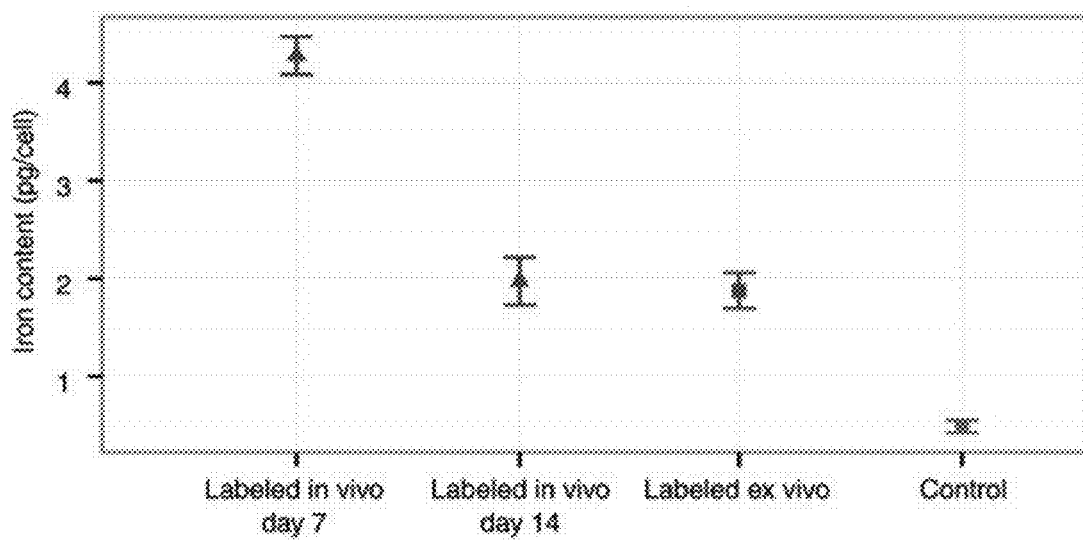
Figure 6:
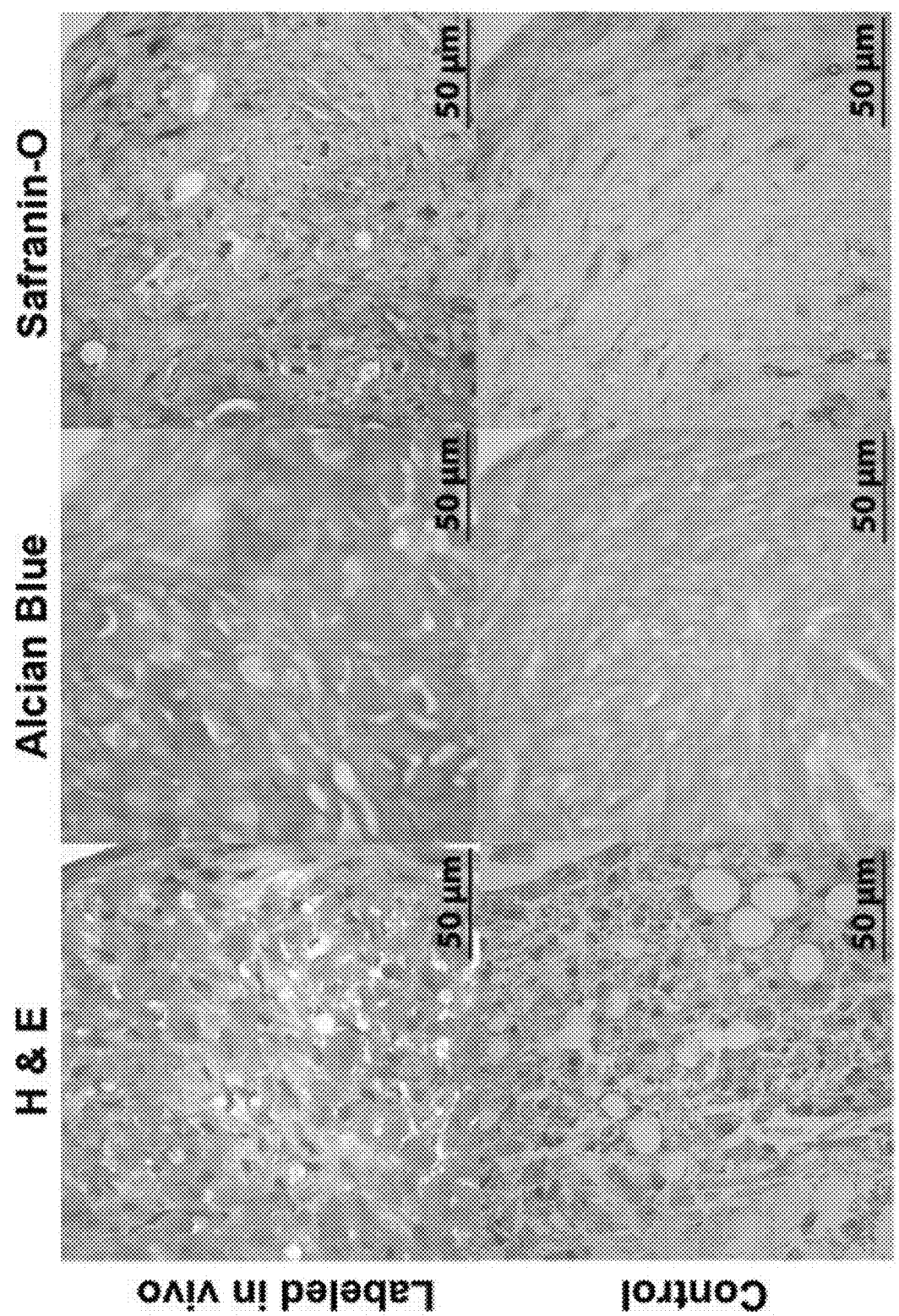
FIG. 6 shows according to an exemplary embodiment of the invention that in vivo-labeled MSCs maintain their chondrogenic differentiation potential in vitro. MSC pellets after differentiation in chondrogenic media for 4 weeks maintain a 3D structure, as shown by hematoxylin-eosin (H & E) stains. Alcian blue- and safranin O-positive stains confirm chondrogenic matrix production for both in vivo-labeled cells and control cells.

In vivo-labeled MSCs displayed strong signal intensity effects on T2-weighted MR images with significantly shortened T2 relaxation times (mean, 8.292 msec+/−6 2.326) compared with un-labeled control cells (mean, 33.614 msec 6 5.111; P=0.024) (FIG. 5A). Follow up studies demonstrated a slow decline in T2 signal intensity effects of labeled MSCs over time, which corresponded to a slow decline in cellular iron content (FIGS. 5A-C). After 3 weeks of cell culture, the T2 signal intensity of in vivo-labeled MSCs was not significantly different from that of unlabeled control cells (P=0.167) (FIG. 5B). A two-way analysis of variance confirmed that differences between groups (F=52.75; df=1, 20; P=0.00000002) and between weeks (F=20.99; df=1, 20; P=0.00006) and the interaction between the two (F=6.29; df=1, 20; P=0.017) were all significant. Accordingly, the iron uptake per cell, as measured by inductively coupled plasma optical emission spectrometry, was significantly higher for in vivo-labeled MSCs at day 7 (at day of transplantation, mean was 4.276 pg per cell+/−0.190) compared with unlabeled cells (mean, 0.490 pg per cell+/−0.063; P, 0.0001) and ex vivo-labeled cells (mean, 1.877 pg per cell+/−6 0.183; P<0.0001) (FIG. 5B). Labeled cells at day 14 showed significantly higher iron uptake than unlabeled cells (P=0.02) but not ex vivo-labeled cells (P>0.05) (FIG. 5B). In vivo-labeled MSCs and unlabeled control cells showed no differences in chondrogenic differentiation (FIG. 6).

In Vivo MR Tracking of Ferumoxytol-Labeled MSCs

Figure 7A:
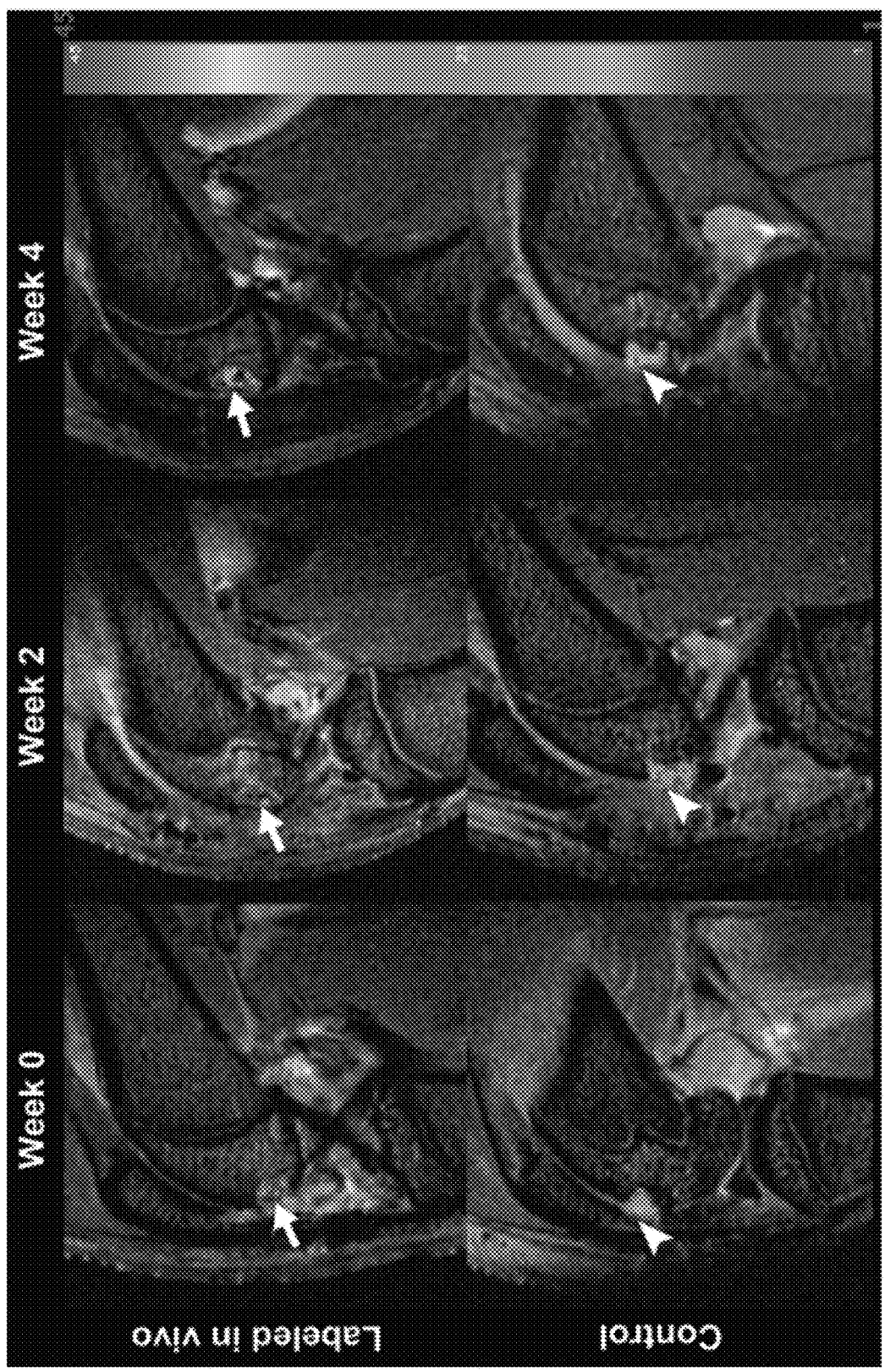
FIGS. 7A-B show according to an exemplary embodiment of the invention that in vivo labeled MSC can be detected on sagittal T2-weighted MR images (4000/15, 30, 45, 60) after implantation in osteochondral defects of rat knee joints.
Figure 7B:
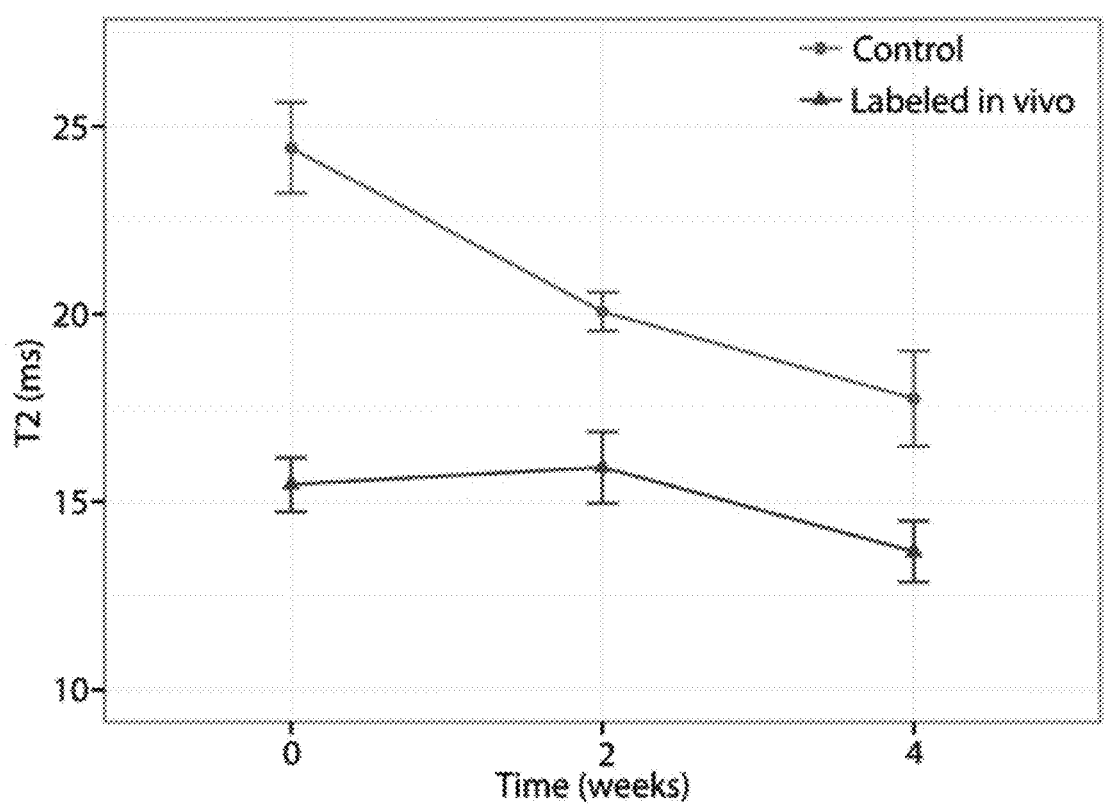

MSCs from ferumoxytol-treated donors, transplanted into osteochondral defects of recipient rats, showed strong signal intensity effects on T2-weighted MR images with significantly shortened T2 relaxation times (mean, 15.459 msec+/−0.729) compared with unlabeled control cells (mean, 24.423 msec+/−1.213 P=0.0002) (FIG. 7). Longitudinal follow-up studies revealed slowly decreasing T2 signal intensity effects of unlabeled control cells over time, apparently because of local cell proliferation and decreasing proton (water) content of the scaffold. Conversely, the T2 signal intensity effects of iron-labeled cells remained stable over time, with the co-efficient on week, $\beta_{week}$, of 20.465 msec+/−0.311 (P=0.152), which may be due to combined effects of decreasing scaffold proton (water) content and slow iron metabolism over time. T2 relaxation times of iron-labeled MSC transplants were significantly lower compared with those of unlabeled control cells at all times of observation (P<0.05) (FIG. 7), although the difference between labeled and unlabeled cells decreased slowly during 4 weeks. A two-way analysis of variance confirmed that differences between groups (F=17.14; df=1, 20; P=0.0005) and between weeks (F=5.60; df=1, 20; P=0.028) and the interaction between the two (F=6.64; df=1, 20; P=0.018) were all significant. A power analysis indicated that future validation studies will need at least five samples in each treatment group to achieve 80% power by using a two-sample t test to detect an effect at week 2 and at least eight samples per treatment group to detect an effect at week 4.

Figure 8:
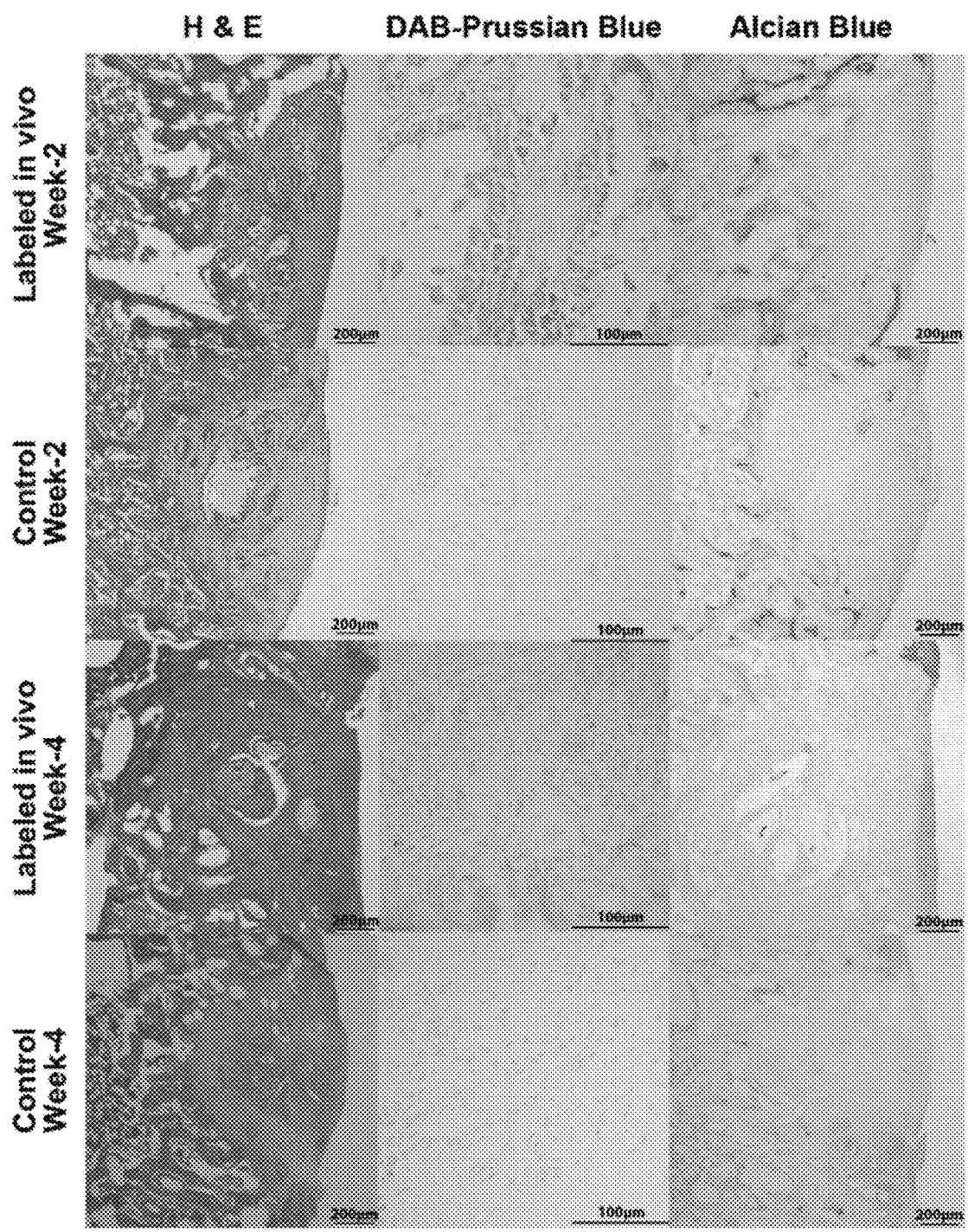
FIG. 8 shows according to an exemplary embodiment of the invention histopathologic correlation of matrix-associated stem cell implants. Representative sections at 2 weeks and 4 weeks after implantation are shown. Hematoxylin-eosin (H & E) stains show engraftment of all implants, and 3,3' diaminobenzidine (DAB)-Prussian blue stains show implanted cells containing iron (brown staining) at 2 and 4 weeks for labeled in vivo transplants, whereas unlabeled control transplants remain unstained. Alcian blue stains show cartilage formation in all implants.
Figure 10:
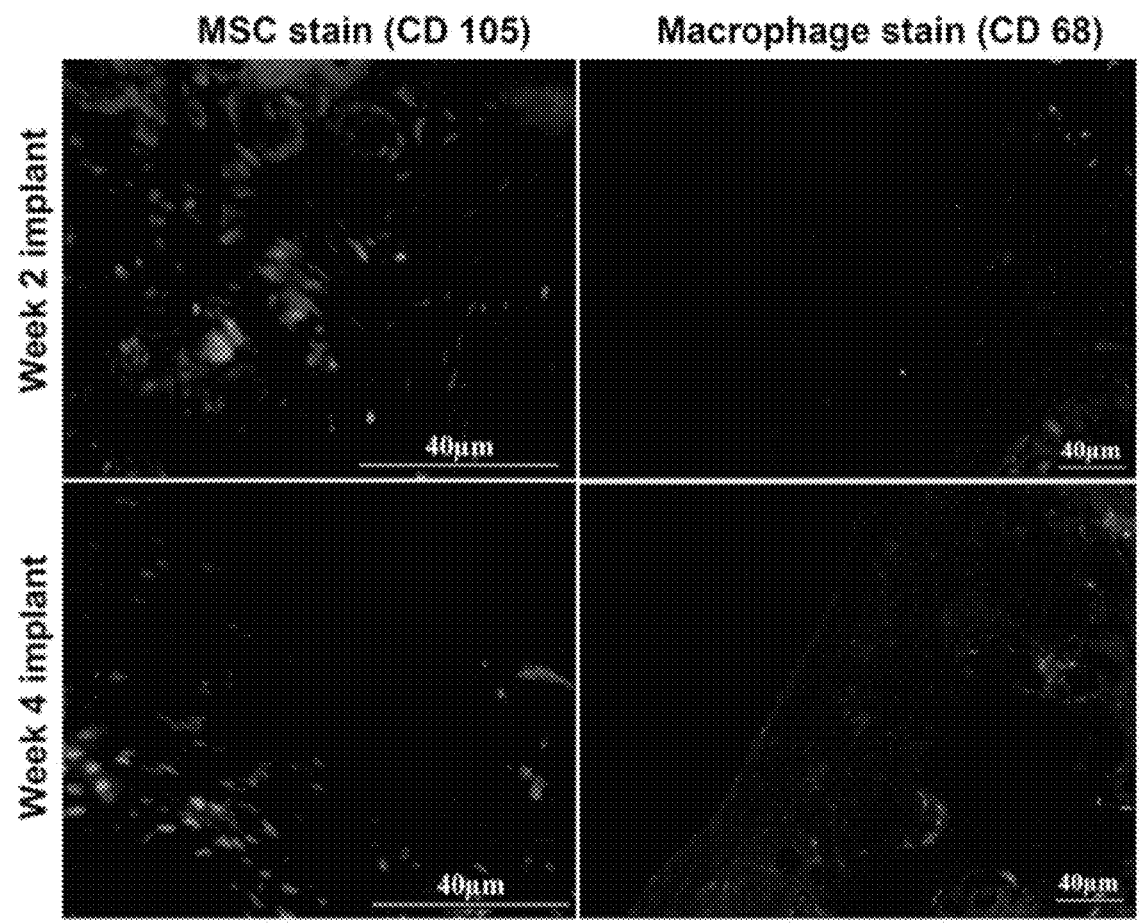
FIG. 10 shows according to an exemplary embodiment of the invention CD105 and CD68 stains of cell implants in osteochondral defects. At week 2 after implantation, there are many CD105 positive MSCs noted in the implant. At week 4, the number of CD105 positive MSC in the implant slightly decreases, consistent with death and initiated differentiation of some of the transplanted cells, while few CD68 macrophages appear in the implant.

Corresponding 3,3' diaminobenzidine-Prussian blue stains confirmed decreasing iron staining of labeled MSC transplants over time, indicating slow iron metabolization (FIG. 8). Hematoxylineosin staining in histopathologic examinations demonstrated engraftment of ferumoxytol-labeled MSCs in the osteochondral defect, without any notable morphologic difference, compared with unlabeled control cells (FIG. 8). At 4 weeks after MSC implantation, both labeled and unlabeled implants had started to remodel the defect and to produce a chondrogenic matrix, as evidenced by staining that was positive for Alcian blue (FIG. 8). A stain that was positive for CD105 for both week 2 and week 4 implants confirmed implantation of MSCs (FIG. 10). Immunohistochemical stains revealed staining that was negative for CD68 for week 2 implants but slightly positive for CD68 surrounding the defect in week 4 implants, suggesting minimal host macrophage influx (FIG. 10).

Synthesis of FITC-Conjugated Ferumoxytol

The carboxydextran coated ferumoxytol nanoparticles were first cross-linked with epichlorohydrin for better stability in vivo as described previously (93), then dialysis to remove low molecular weight compounds against water using dialysis tubing (12-14K cutoff) over three days yielded cross-linked iron oxide nanoparticles (CLIO). The obtained amine-presenting nanoparticles in PBS buffer were then reacted with a DMSO solution of Fluorescein isothiocyanate (1:8 CLIO:FITC molar ratio). Purification with Microcon® centrifuge filters ($^{10}$K cutoff, 5 mL→0.2 mL volume reduction, 4600 rpm, PBS buffer addition and centrifugation) was repeated 10 times until the filtrate had no fluorescence to afford a purified product CLIO-FITC. Each nanoparticle on average had 3.8 Fluorescein molecules. The amount of FITC covalently linked to a nanoparticle was calculated using two methods. In the first method, FITC concentration was determined by subtracting the maximum absorption (492 nm) of CLIO-FITC from the absorbance of unconjugated TNP alone (measured for CLIO-NH2 at the same concentration of iron) and dividing the result by known extinction coefficient of FITC (70,000 $M^{-1}$ $cm^{-1}$) at 492 nm. In the second method, the FITC's emission peak of a diluted (to avoid fluorescence self-quenching) CLIO-FITC was integrated and its concentration was estimated using a calibration plot obtained for a set of standard FITC solutions. Both methods gave consistent results (less than 8% difference) for three different solutions of CLIO-ICT.

Remarks

It is noted that the in vivo method does not use any additional transfection agents as is common in ex vivo approaches. In other words, MSCs efficiently phagocytose ferumoxytol without transfection agents in vivo. However, it is noted that MSCs do not phagocytose ferumoxytol ex vivo with high enough efficiency to enable in vivo tracking with MR imaging.

It is still further noted that the in vivo method does not require any ex vivo manipulations to the harvested stem cells. This is important for translational efforts.

It is further noted that other studies showed uptake of iron oxide nanoparticles by bone marrow macrophages in animal models and in patients. These iron-labeled macrophages migrate into apoptotic stem cell transplants, which can be used for detection of stem cell death and/or rejection. Macrophages migrate to much lesser extent into viable transplants, which was below detection limits of our cellular MR imaging test.

It is still further noted that the in vivo method does not use any ex vivo labeling as is common in ex vivo methods of stem cell labeling.

It is still further noted that the in vivo method eliminates risks of contamination and biologic alteration of bone marrow-derived stem cells caused by ex vivo-labeling procedures and that the method could be immediately applied in a clinical setting for in vivo tracking of bone marrow-derived stem cells in arthritic joints or other target tissues.

What is claimed is:

1. A method for in vivo and noninvasive monitoring of stem cell implants, comprising:
    (a) intravenously injecting iron oxide nanoparticles into a subject to achieve in vivo phagocytotic iron labeling of stem cells;
    (b) harvesting from bone marrow of said subject the in vivo iron labeled stem cells;
    (c) directly after harvesting, without ex vivo iron labeling of the stem cells, transplanting harvested in vivo iron labeled stem cells into a different subject; and
    (d) monitoring in vivo and noninvasively the transplanted in vivo iron labeled stem cells using magnetic resonance imaging.

2. The method as set forth in claim 1, wherein the stem cells are mesenchymal stem cells.

3. The method as set forth in claim 1, wherein the harvesting takes place in about one to three days from the intravenous injection.

4. The method as set forth in claim 1, wherein the intravenous injection of the iron oxide nanoparticles is dosed at 28 mg of iron per kg of body weight of the subject.

5. The method as set forth in claim 1, wherein the intravenous injection of the iron oxide nanoparticles is dosed at 5-10 mg of iron per kg of body weight of the subject.

6. The method as set forth in claim 1, wherein the harvested stem cells are transplanted in an organ of a different subject.

7. The method as set forth in claim 1, wherein the harvested stem cells are transplanted in a joint, a brain, a heart, a liver or a pancreas of a different subject.

8. The method as set forth in claim 1, wherein the in vivo phagocytotic iron labeling of stem cells occurs in vivo without the use of a transfection agent.

9. The method as set forth in claim 1, wherein the method does not use any ex vivo labeling or ex vivo manipulations to the stem cells.

* * * * *